(12) United States Patent
Shibata et al.

(10) Patent No.: US 11,014,887 B2
(45) Date of Patent: May 25, 2021

(54) METHOD OF PRODUCING PENTAFLUOROSULFANYL AROMATIC COMPOUND

(71) Applicant: UBE INDUSTRIES, LTD., Yamaguchi (JP)

(72) Inventors: Norio Shibata, Aichi (JP); Norimichi Saito, Yamaguchi (JP)

(73) Assignee: UBE INDUSTRIES, LTD.

( * ) Notice: Subject to any disclaimer, the term of this patent is extended or adjusted under 35 U.S.C. 154(b) by 0 days.

(21) Appl. No.: 16/489,275

(22) PCT Filed: Feb. 26, 2018

(86) PCT No.: PCT/JP2018/006884
§ 371 (c)(1),
(2) Date: Aug. 27, 2019

(87) PCT Pub. No.: WO2018/159515
PCT Pub. Date: Sep. 7, 2018

(65) Prior Publication Data
US 2020/0062709 A1 Feb. 27, 2020

(30) Foreign Application Priority Data
Feb. 28, 2017 (JP) ............................... JP2017-037356

(51) Int. Cl.
*C07D 213/71* (2006.01)
*C07C 381/00* (2006.01)
*C07D 239/38* (2006.01)
*C07D 277/76* (2006.01)

(52) U.S. Cl.
CPC .......... *C07D 213/71* (2013.01); *C07C 381/00* (2013.01); *C07D 239/38* (2013.01); *C07D 277/76* (2013.01)

(58) Field of Classification Search
CPC .. C07C 381/00; C07D 213/71; C07D 239/38; C07D 277/76
See application file for complete search history.

(56) References Cited

U.S. PATENT DOCUMENTS

| | | | | |
|---|---|---|---|---|
| 2010/0130790 A1* | 5/2010 | Umemoto | ............. | C07C 381/00 568/74 |
| 2011/0166392 A1* | 7/2011 | Umemoto | ............. | C07C 381/00 568/74 |
| 2011/0306798 A1* | 12/2011 | Umemoto | ............. | C07C 381/00 568/74 |
| 2013/0324765 A1* | 12/2013 | Umemoto | ............... | A61P 33/06 568/74 |

OTHER PUBLICATIONS

Cui et al., "IF5 affects the final stage of the Cl—F exchange fluorination in the synthesis of pentafluoro-λ6-electron-withdrawing substituents", Chem. Commun., 2017, 53, 5997-6000.
International Search Report for PCT/JP2018/006884, dated May 22, 2018, 2 pages.
Kanishchev et al., "Synthesis and Characterization of 2-Pyridylsulfur Pentafluorides", Angew. Chem. Int. E. 2015, 54, 280-284.
Kosobokov et al., "Importance of a Fluorine Substituent for the Preparation of meta- and para-Pentafluoro-λ6-sulfanyl-Substituted Pyridines", Angew. Chem. Int. Ed. 2016, 55, 10781-10785.
Sipyagin et al., "Synthesis of Pyridines with Fluoro-Containing Superlipophilic Substituents", J. Fluorine Chem., 1995, 54: 115.
Umemoto et al., "Discovery of practical production processes for arylsulfur pentafluorides and their higher homologues, bis- and tris (sulfur pentafluorides): Beginning of a new era of "super-trifluoromethyl" arene chemistry and its industry", Beilstein J. Org. Chem. 2012, 8, 461-471.
Sipyagin et al., "Synthesis of Pyridines with Fluoro-Containing Superlipophilic Substituents", J. Fluorine Chem., 1991, 54: 115.
English translation of Office action for CN Application 201880013839. 5, dated Dec. 9, 2020, 1 page.

\* cited by examiner

*Primary Examiner* — Deepak R Rao
(74) *Attorney, Agent, or Firm* — Adsero IP

(57) ABSTRACT

A method of producing a pentafluorosulfanyl aromatic compound is provided. A method of producing a pentafluorosulfanyl aromatic compound represented by general formula (3):

$$Ar-(SF_5)_k \qquad (3)$$

where Ar is a substituted or an unsubstituted aryl group or heteroaryl group, and k is an integer of 1 to 3;
the method includes reacting $IF_5$ with a halotetrafluorosulfanyl aromatic compound represented by general formula (2):

$$Ar-(SF_4Hal)_k \qquad (2)$$

where Ar and k are defined as above; and Hal is a Cl group, a Br group, or an I group.

7 Claims, No Drawings

METHOD OF PRODUCING PENTAFLUOROSULFANYL AROMATIC COMPOUND

CROSS-REFERENCE TO RELATED APPLICATION

This application claims priority to and is a 35 U.S.C. § 371 national phase application of PCT/JP2018/006884 (WO2018/159515), filed on Feb. 26, 2018, entitled "METHOD FOR PRODUCING PENTAFLUOROSULFANYL AROMATIC COMPOUND", which application claims priority to and the benefit of Japanese Patent Application No. 037356/2017, filed Feb. 28, 2017, the disclosures of which are incorporated herein by reference in their entirety.

TECHNICAL FIELD

The present invention relates to a method of producing a pentafluorosulfanyl aromatic compound.

BACKGROUND ART

A pentafluorosulfanyl group (hereinafter, referred to as $SF_5$ group) has been drawing attention as a very promising material. For the unique physicochemical characteristics, the $SF_5$ group is attracting attention especially in the pharmaceutical field. The $SF_5$ group is often compared with a well-known $CF_3$ group. The electronegativity of the $SF_5$ group is 3.65, which is close to the electronegativity of a nitro group, whereas the electronegativity of the $CF_3$ group is 3.36. The size of the $SF_5$ group is approximately intermediate between those of a $CF_3$ group and a tert-butyl group. Although both the $SF_5$ group and the $CF_3$ group have high electronegativity and hydrophobicity (Hansh hydrophobic constant $\pi$ ($CF_3$) of 1.09 and $\pi$ ($SF_5$) of 1.51), their properties are generally different. The $SF_5$ group exhibits lipophilicity, membrane permeability, and metabolic stability. Due to these characteristics, the $SF_5$ group may be potentially useful for new drug candidate compounds, herbicides, insecticides, antidepressants, and antimalarial drugs, for example. Non-Patent Literature (NPL) 1 discloses a two-step reactions (scheme 1a) for obtaining $Ar-SF_5$ by oxidatively chlorinating and fluorinating an aryl disulfide, followed by Cl—F exchange reactions ($S_N$ reactions) of the resulting $Ar-SF_4Cl$ with a fluorinating agent, such as $ZnF_2$, HF, or Sb(III/V) fluoride. This process is currently put into practical use.

Moreover, regarding pyridines (Py) having a $SF_5$ group, NPL 2 discloses a method of obtaining o-Py-$SF_5$ by oxidative chlorination and fluorination of dipyridyl disulfide, followed by Cl—F exchange reactions in which the resulting o-Py-$SF_4Cl$ is reacted with AgF (scheme 1b). In NPL 2, fluorination of o-Py-$SF_4Cl$ having a 5-$NO_2$ or 5-$CF_3$ group by using AgF was attempted, but little or no Py-$SF_5$ was synthesized.

NPL 3 discloses a synthetic method for m-Py-$SF_5$ and p-Py-$SF_5$ (scheme 1c). The reason that Cl—F exchange reactions do not proceed in o-Py-$SF_4Cl$ is presumably because C—S bond cleavage (pathway a in scheme 1c) due to competitive nucleophilic aromatic substitution ($S_NAr$) reactions preferentially occurs relative to Cl—F exchange reactions (pathway b in scheme 1c) via $S_N$ reactions. It is known that Cl—F exchange reactions are difficult to proceed in electron-deficient $SF_4Cl$ group-containing aromatic compounds. NPL 1 discloses that Cl—F exchange reactions did not proceed well even by reacting p-$NO_2$-phenyl-$SF_4Cl$ with $ZnF_2$ at a high temperature and the yield of p-$NO_2$-phenyl-$SF_5$ was 36%.

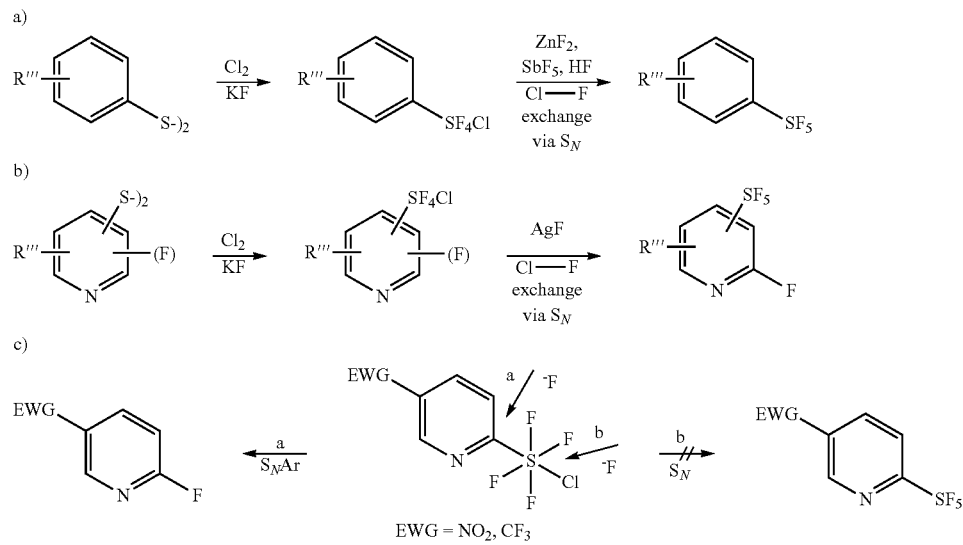

NPL 4 discloses that thiopyridines having Cl substituents are reacted with $IF_5$.

CITATION LIST

Non Patent Literature

NPL 1: T. Umemoto, L. Garrick, N. Saito, Beilstein J. Org. Chem., 2012, 8, 461

NPL 2: O. S. Kanishchev, W. R. Dolbier, Jr., Angew. Chem. Int. Ed., 2015, 54, 280

NPL 3: M. Kosobokov, B. Cui, A. Balia, K. Matsuzaki, E. Tokunaga, N. Saito, N. Shibata, Angew. Chem. Int. Ed., 2016, 55, 10781

NPL 4: A. Sipyagin, I. Pomytkin, S. Paltsun, N. Aleinikov and V. Kartsev, J. Fluorine Chem., 1991, 54, 115

SUMMARY OF INVENTION

Technical Problem

Efficient production of a pentafluorosulfanyl aromatic compound by conventional methods is subjected to restrictions as to the substituents and the like. NPL 4 discloses a scheme in which pentafluorosulfanylpyridines are produced by reacting pyridinethiols with $IF_5$. However, as described hereinafter, the present inventors actually attempted this reaction and confirmed that the reaction did not proceed. In view of the above, an object of the present invention is to provide a method of efficiently producing a $SF_5$ group-containing aromatic compound regardless of the substituents.

Solution to Problem

The present inventors found that $IF_5$ allows the above-described reaction to proceed smoothly. In other words, the above-mentioned object is attained by the following present invention.
[1] A method of producing a pentafluorosulfanyl aromatic compound represented by general formula (3), including reacting $IF_5$ with a halotetrafluorosulfanyl aromatic compound represented by general formula (2).
[2] The method according to [1], where the aryl group or heteroaryl group has a substituent selected from the group consisting of a halogen group, an electron-withdrawing group excluding halogen groups, and an electron-donating group excluding halogen groups.
[3] The method according to [1], where the halotetrafluorosulfanyl aromatic compound and the pentafluorosulfanyl aromatic compound are represented by general formulae (2') and (3'), respectively.
[4] The method according to [1], where the substituent is an electron-withdrawing group excluding halogen groups, and the reaction is performed at 50° C. or higher.
[5] The method according to [1], where the substituent is an electron-withdrawing group excluding halogen groups, and 1 equivalent or more of $IF_5$ is used for the $SF_4Hal$ group, that is the halotetrafluorosulfanyl aromatic compound represented by general formula (2).
[6] The method according to [3], where at least one of X and Y is N; and at least one of R is an electron-withdrawing group, excluding halogen groups, that is present at the 3-position of the ring.
[7] The method according to [1], where the halotetrafluorosulfanyl aromatic compound and the pentafluorosulfanyl aromatic compound are represented by general formulae (2'') and (3''), respectively.

Advantageous Effects of Invention

According to the present invention, it is possible to produce a pentafluorosulfanyl aromatic compound.

DESCRIPTION OF EMBODIMENTS

In the present invention, the wording "X to Y" includes the lower and the upper limit values of X and Y, and the wording "X or Y" includes either X or Y, or both. Hereinafter, the present invention will be described in detail.

1. Production Method of Present Invention

The present invention includes the following reaction step.

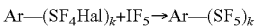

(1) Halotetrafluorosulfanyl Aromatic Compounds
A halotetrafluorosulfanyl aromatic compound is represented by general formula (2): $Ar—(SF_4Hal)_k$. Ar is a substituted or unsubstituted aryl group or a substituted or unsubstituted heteroaryl group. The aryl group is an aromatic hydrocarbon group, and examples include a phenyl group and a naphthyl group. The heteroaryl group is a heteroaromatic hydrocarbon group, and examples include a pyridyl group, a pyrimidyl group, an indolyl group, and a benzothiazolyl group.

Examples of a substituent of the aryl group and the heteroaryl group (hereinafter, also collectively referred to as "Ar group") include (i) a halogen group, (ii) an electron-withdrawing group excluding halogen groups, and (iii) an electron-donating group excluding halogen groups. Examples of the halogen group include a F group, a Cl group, a Br group, and an I group. However, a F group, a Cl group, and a Br group are preferable in view of easy availability.

The electron-withdrawing group is a group having properties that readily withdraw electrons relative to hydrogen. In the present invention, the electron-withdrawing group is preferably a group having a positive substituent constant σ value determined by the Hammett equation. Examples of the electron-withdrawing group include a $CF_3$ group, a $CCl_3$ group, a $CBr_3$ group, a $CI_3$ group, a nitro group ($NO_2$ group), a cyano group (CN group), a COOH group, $COOR^1$ group ($R^1$ is an alkyl group having 1 to 3 carbon atoms), an $SO_3H$ group, and an $SO_3R^2$ group ($R^2$ is an alkyl group having 1 to 3 carbon atoms or a perfluoroalkyl group having 1 to 3 carbon atoms). Among these groups, a fluorine-containing group is preferable. Examples of the fluorine-containing group include a $CF_3$ group and an $SO_3CF_3$ group. Further, among these electron-withdrawing groups, a nitro group, a $CF_3$ group, or a cyano group is also preferable. In general, halogen groups are also classified as electron-withdrawing groups. However, in some cases, halogen groups behave like electron-donating groups due to the mesomeric effect and the like. Accordingly, the electron-withdrawing group in the present invention excludes halogen groups. Hereinafter, the electron-withdrawing group excluding halogen groups is also simply referred to as an "electron-withdrawing group".

The electron-donating group is a group having properties that readily donate electrons relative to hydrogen. In the present invention, the electron-donating group is preferably a group having a negative substituent constant σ value determined by the Hammett equation. Examples of the electron-donating group include an alkyl group, an alkoxy group, a hydroxy group, and an amino group. The alkyl group is preferably a linear, branched, or cyclic alkyl group having 1 to 18 carbon atoms, and an alkyl group having 1 to 5 carbon atoms is preferable. The same applies to an alkyl group within the alkoxy group. For the same reason described above, the electron-donating group in the present invention excludes halogen groups. Hereinafter, the electron-donating group excluding halogen groups is also simply referred to as an "electron-donating group".

The substituents (i), (ii), and (iii) may coexist within a compound. As described hereinafter, however, preferable reaction conditions are different depending on the characteristics of substituents. Accordingly, these substituents do not coexist within a compound in one embodiment. However, in another embodiment, the substituents (i) and (iii) coexist within a compound since the substituents (i) and (iii) share similar characteristics.

Hal is a Cl group, a Br group, or an I group, and a Cl group is preferable in view of easy availability.

k represents the number of the SF$_4$Hal group. k is an integer of 1 to 3, preferably 1 or 2, and more preferably 1.

The halotetrafluorosulfanyl aromatic compound is preferably represented by general formula (2').

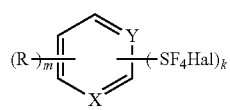

(2')

X is C or N, and Y is C or N. The number of N on the ring is represented by n, and n is an integer of 0 to 2. k is defined as above.

R is a substituent of the ring, and m represents the number of R. R is preferably the above-described substituent (i), (ii), or (iii). When m is not 0, a plurality of R may be the same or different. m is represented by 0 to (5–k–n). In other words, m can be a value of 0 to 5.

When N exists in formula (2') and an electron-withdrawing group is present at the 3-position based on N, the effects of the present invention becomes further remarkable.

In another embodiment, the halotetrafluorosulfanyl aromatic compound is preferably represented by general formula (2").

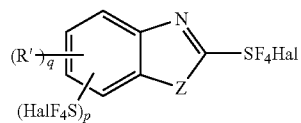

(2")

Z is N or S, and Hal is defined as above. p represents the number of the SF$_4$Hal group on the six-membered ring. p is an integer of 0 to 2, preferably 0 or 1, and more preferably 0.

R' is a substituent of the six-membered ring, and q represents the number of R'. R' is preferably the above-described substituent (i), (ii), or (iii). When q is not 0, a plurality of R' may be the same or different. q is an integer represented by 0 to (4–p) and can be 0 to 4.

(2) IF$_5$

Iodine pentafluoride (IF$_5$) converts the SF$_4$Hal group of the halotetrafluorosulfanyl aromatic compound into a F group. The amount of IF$_5$ used is not limited provided that a target compound is obtained and is preferably 0.1 equivalent or more and more preferably 2 equivalents or more, relative to the SF$_4$Hal group. The upper limit of the amount used is preferably 10 equivalents or less in view of costs and the like.

(3) Pentafluorosulfanyl Aromatic Compounds

The pentafluorosulfanyl aromatic compound obtained by the production method of the present invention is represented by general formula (3): Ar—(SF$_5$)$_k$. Ar is the same as Ar in general formula (2). k represents the number of the SF$_5$ group. k is an integer of 1 to 3, preferably 1 or 2, and more preferably 1. The pentafluorosulfanyl aromatic compound is preferably represented by general formula (3').

(3')

X, Y, R, m, and k are defined as in general formula (2').

In another embodiment, the pentafluorosulfanyl aromatic compound is preferably represented by general formula (3").

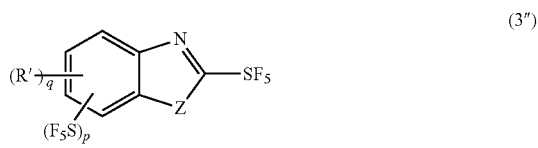

(3")

Z, R', p, and q are defined as in general formula (2").

Specific examples of the pentafluorosulfanyl aromatic compound are shown below.

3c

3d

3e

3f

3g

3h

3i

3n

-continued

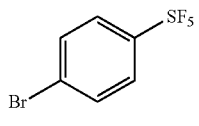
3o

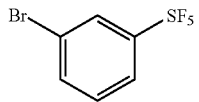
3p

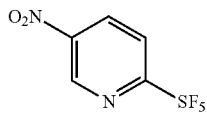
3a

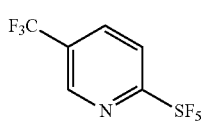
3b

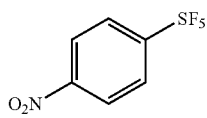
3j

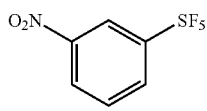
3k

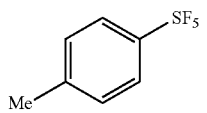
3l

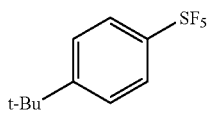
3m (4) Reaction Conditions

The reaction conditions may be appropriately adjusted to achieve a desirable yield. Hereinafter, preferable conditions will be described.

1) Cases in which the Ar Group has No Substituent or has as a Substituent (i) a Halogen Group or (iii) the Above-Described Electron-Donating Group The reaction temperature is not particularly limited and is preferably room temperature (20° C.) or higher. The upper limit of the temperature is also not limited but is preferably 100° C. or lower.

The amount of $IF_5$ used is also not limited and is preferably 0.1 equivalent or more, more preferably 1 equivalent or more, and further preferably 2 equivalents or more, relative to the $SF_4Hal$ group. The upper limit is also not limited, but is preferably 10 equivalents or less and more preferably 8 equivalents or less from economic and other viewpoints.

The reactions may be performed with or without a solvent. Solvent-free reactions are possible since $IF_5$ is a liquid. For such solvents, halogen-free solvents are preferable, and nonpolar solvents, such as hexane, are more preferable.

2) Cases in which the Ar Group has (ii) the Above-Described Electron-Withdrawing Group as a Substituent The reaction temperature is preferably 50° C. or higher and more preferably 60° C. or higher. The upper limit of the reaction temperature is preferably 100° C. or lower and more preferably 80° C. or lower.

The amount of $IF_5$ used is also not limited and is preferably 2 equivalents or more, more preferably 3 equivalents or more, and further preferably 5 equivalents or more, relative to the $SF_4Hal$ group. The upper limit is also not limited, but is preferably 10 equivalents or less and more preferably 8 equivalents or less in view of costs and the like.

The reactions may be performed with or without a solvent. Solvent-free reactions are possible since $IF_5$ is a liquid. For such solvents, nonpolar solvents are preferable, and examples include halogen-free solvents and hydrocarbon solvents, such as hexane.

EXAMPLES

[Example 1 and Comparative Example 1] Compound Having an Electron-Withdrawing Group as a Substituent The following reaction was performed by using a fluorinating agent.

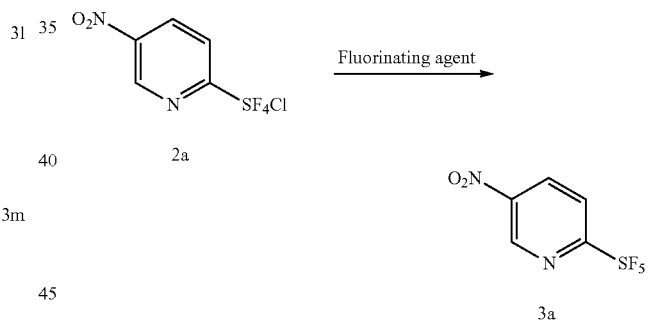

Specifically, 5-nitro-o-chlorotetrafluorosulfanylpyridine (0.72 mmol) prepared by a published method was charged to a fluoro-polymer vessel inside a glove box. Under a nitrogen gas stream, $IF_5$, whose charging amount was shown in Table 1, was transferred to a cylinder for weighing, and then was fed to the vessel through a Teflon (registered trademark) tube. The reaction mixture was stirred under the conditions shown in Table 1. After the reaction was completed, cold water was poured into the reaction mixture, and the obtained reaction solution was neutralized with an aqueous solution of sodium bicarbonate. The water layer was extracted with 3 mL of hexane three times, and the obtained organic layer was dried over sodium sulfate. Subsequently, the organic layer was filtered, and the filtrate was concentrated under reduced pressure to remove solvent, and the residue was purified through silica gel column chromatography (pentane/dichloromethane) to yield the target compound. The yield was determined by $^{19}F$-NMR analysis (fluorobenzene used as an internal standard).

TABLE 1

|  |  | Fluorinating agent | (eq.) | Temperature (° C.) | Time (h) | Solvent | Yield (%) |
|---|---|---|---|---|---|---|---|
| Comp. Ex. | 1-1 | $ZnF_2$ | 0.6 | 80 | 12 | none | 0 |
|  | 1-2 | $CuF_2$ | 0.6 | 80 | 12 | none | 0 |
|  | 1-3 | $TiF_4$ | 0.4 | 80 | 12 | none | 0 |
|  | 1-4 | DMPU•HF | 3 | 55 | 3 | none | 0 |
|  | 1-5 | Py•HF | 3 | 55 | 3 | none | 0 |
|  | 1-6 | AgF | 2 | 60 | 48 | none | 0 |
|  | 1-7 | $IF_5$•Py•HF | 3 | 50 | 14 | $CH_2Cl_2$ | 0 |
|  | 1-8 | $IF_5$•Py•HF | 3 | 50 | 40 | none | 0 |
| Ex. | 1-1 | $IF_5$ | 3 | r.t. | 40 | none | trace |
|  | 1-2 | $IF_5$ | 2 | 65 | 14 | none | 1 |
|  | 1-3 | $IF_5$ | 3 | 65 | 14 | none | 43 |
|  | 1-4 | $IF_5$ | 4 | 65 | 14 | none | 57 |
|  | 1-5 | $IF_5$ | 5 | 65 | 14 | none | 97 (88)* |
|  | 1-6 | $IF_5$ | 6 | 65 | 14 | none | 95 |
|  | 1-7 | $IF_5$ | 5 | 40 | 17 | $CH_2Cl_2$ | 0 |
|  | 1-8 | $IF_5$ | 5 | 65 | 17 | hexane | 46 |
|  | 1-9 | $IF_5$ | 0.5 | 80 | 48 | none | 0 |

*isolated yield

[Example 2] Compounds Having Electron-Withdrawing Groups as Substituents

The following reaction was performed in a similar manner to Example 1 by using various chlorotetrafluorosulfanyl aromatic compounds (0.72 mmol) as starting materials. Here, the neat reaction was performed, in other words, the reaction was performed without using a solvent. The scheme and the results are shown in Table 2.

TABLE 2

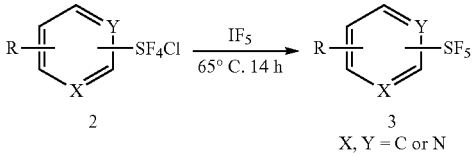

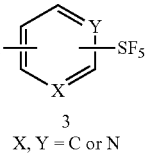

|  | 3a | 3b | 3j | 3k |
|---|---|---|---|---|
| Amount of $IF_5$ (equiv) | 5 | 5 | 3 | 3 |
| Yield (%) | 88(97) | 81(89) | 75(89) | 82(91) |

The isolated yields are shown. The numerical values in the parentheses are yields obtained by $^{19}$F-NMR analysis (fluorobenzene used as internal standard). Table 2 clearly reveals that the target compounds can be obtained in high yield.

[Example 3] Compounds Having Halogen Groups as Substituents

The following reaction was performed in a similar manner to Example 2 by using various chlorotetrafluorosulfanyl aromatic compounds as starting materials. The scheme and the results are shown in Table 3.

TABLE 3

R—[ring with X,Y]—SF$_4$Cl  →(IF$_5$, 65° C. 14 h)→  R—[ring with X,Y]—SF$_5$ 2    3
X, Y = C or N Structures: 3c, 3d, 3e, 3f, 3g*, 3h, 3i

| | 3c | 3d | 3e | 3f | 3g* | 3h | 3i |
|---|---|---|---|---|---|---|---|
| Amount of IF$_5$ (equiv) | 3 | 3 | 3 | 3 | 1.5 | 5 | 5 |
| Amount of Comp. 2 (mmol) | 0.72 | 0.72 | 0.72 | 0.72 | 4.9 | 0.72 | 0.72 |
| Yield (%) | 56(70) | 68(80) | 71(97) | 45(53) | 20 | 27(48) | 42(50) |

*85° C. × 24 h

The isolated yields are shown. The numerical values in the parentheses are yields obtained by $^{19}$F-NMR analysis (fluorobenzene used as internal standard). Table 3 clearly reveals that the target compounds can be obtained in high yield.

[Example 4] Compounds Having Halogen Groups as Substituents

The following reaction was performed in a similar manner to Example 1 by using various chlorotetrafluorosulfanyl aromatic compounds as starting materials. The scheme and the results are shown in Table 4 below.

TABLE 4

$R^a$—[ring]—SF$_4$Cl  →(IF$_5$ (0.2 equiv), r.t. 12 h)→  $R^a$—[ring]—SF$_5$
$R^b$                                                    $R^b$ 2            3
1.8 mmol

| $R^a$ | H | H | Br |
|---|---|---|---|
| $R^b$ | Cl | Br | H |
| | 3n | 3o | 3p |
| Yield (%) | 82(90) | 77(88) | 43(61)* |

*reaction in the presence of 0.5 equiv of Ag$_2$CO$_3$

The isolated yields are shown. The numerical values in the parentheses are yields obtained by $^{19}$F-NMR analysis (fluorobenzene used as internal standard). Table 4 clearly reveals that the target compounds can be obtained in high yield.

[Example 5] Compounds Having Electron-Donating Groups as Substituents

The following reaction was performed in a similar manner to Example 4 by using various chlorotetrafluorosulfanyl aromatic compounds as starting materials. The scheme and the results are shown in Table 5 below.

TABLE 5

$R^a$—[ring]—SF$_4$Cl  →(IF$_5$ (0.2 equiv), r.t. 12 h)→  $R^a$—[ring]—SF$_5$
$R^b$                                                    $R^b$ 2            3
1.8 mmol

| $R^a$ | H | H |
|---|---|---|
| $R^b$ | Me | t-Bu |
| | 3l | 3m |
| Time (h) | 5 | 24 |
| Yield (%) | 28(35) | 41(59) |
| | 50(67)* | |

*reaction in the presence of 0.5 equiv of Ag$_2$CO$_3$ for 12 h

The isolated yields are shown. The numerical values in the parentheses are yields obtained by $^{19}$F-NMR analysis (fluorobenzene used as internal standard). Table 5 clearly reveals that the target compounds can be obtained in high yield. For the synthesis of Compound 3l, the reaction was also performed in the presence of 0.5 equivalent of silver carbonate. As a result, the yield was enhanced through suppressed side reactions.

Example 6

The following reaction was performed under conditions and the like similar to Example 2. The scheme and the result are shown in Table 6.

TABLE 6

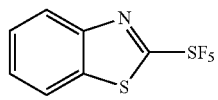

| Example | Target compound | Amount of IF$_5$ used (equiv) | Yield (%) |
|---|---|---|---|
| 6-1 | 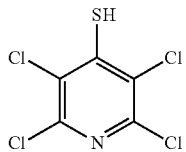 [SMILES: Sc1c(Cl)c(Cl)nc(Cl)c1Cl] | 5 | 28 |

Comparative Example 2

The reaction disclosed in NPL 4 was performed. Specifically, 99.6 mg of a pyridinethiol shown below and 10 equivalents of IF$_5$ were stirred in the absence of a solvent at 70° C. overnight. As a result, however, a compound having a SF$_5$ group, which had been converted from the SH group, was hardly observed.

According to the production method of the present invention, it is possible to efficiently produce a pentafluorosulfanyl aromatic compound.

The invention claimed is:

1. A method of producing a pentafluorosulfanyl aromatic compound represented by general formula (3):

Ar—(SF$_5$)$_k$     (3)

wherein Ar is a substituted or an unsubstituted aryl group or heteroaryl group and
k is an integer of 1 to 3;
the method comprising reacting IF$_5$ with a halotetrafluorosulfanyl aromatic compound represented by general formula (2):

Ar—(SF$_4$Hal)$_k$     (2)

wherein Ar and k are defined as above; and
Hal is a Cl group, a Br group, or an I group.

2. The method according to claim 1, wherein the aryl group or heteroaryl group has a substituent selected from the group consisting of a halogen group, an electron-withdrawing group excluding halogen groups, and an electron-donating group excluding halogen groups.

3. The method according to claim 1, wherein the halotetrafluorosulfanyl aromatic compound and the pentafluorosulfanyl aromatic compound are represented by general formulae (2') and (3'), respectively:

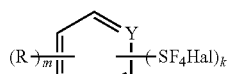     (2')

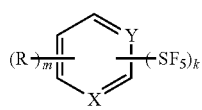     (3')

wherein: Hal is a Cl group, a Br group, or an I group;
X is C or N;
Y is C or N;
R is each independently a halogen group, an electron-withdrawing group excluding halogen groups, or an electron-donating group excluding halogen groups;
k is an integer of 1 to 3;
m is an integer represented by 0 to (5−k−n); and
n is the number of N.

4. The method according to claim 1, wherein the substituent is an electron-withdrawing group excluding halogen groups, and the reaction is performed at 50° C. or higher.

5. The method according to claim 1, wherein the substituent is an electron-withdrawing group excluding halogen groups, and 1 equivalent or more of IF$_5$ is used for the SF$_4$Hal group, that is the halotetrafluorosulfanyl aromatic compound represented by general formula (2).

6. The method according to claim 3, wherein:
at least one of X and Y is N; and
at least one of R is an electron-withdrawing group excluding halogen groups, the electron-withdrawing group being present at the 3-position of the ring.

7. The method according to claim 1, wherein the halotetrafluorosulfanyl aromatic compound and the pentafluorosulfanyl aromatic compound are represented by general formulae (2") and (3"), respectively:

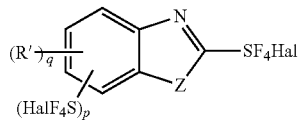     (2")

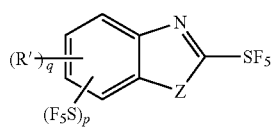     (3")

wherein Hal is a Cl group, a Br group, or an I group;
Z is N or S;
p is an integer of 0 to 2;
R' is each independently a halogen group, an electron-withdrawing group excluding halogen groups, or an electron-donating group excluding halogen groups; and
q is an integer represented by 0 to (4−p).

* * * * *